(12) United States Patent
Link

(10) Patent No.: US 9,393,561 B2
(45) Date of Patent: Jul. 19, 2016

(54) PIPETTING DEVICE AND MULTI-CHANNEL PIPETTING DEVICE

(71) Applicant: Eppendorf AG, Hamburg (DE)

(72) Inventor: Holger Link, Hamburg (DE)

(73) Assignee: EPPENDORE AG, Hamburg, DE (US)

( * ) Notice: Subject to any disclaimer, the term of this patent is extended or adjusted under 35 U.S.C. 154(b) by 446 days.

(21) Appl. No.: 13/782,787

(22) Filed: Mar. 1, 2013

(65) Prior Publication Data

US 2013/0239706 A1    Sep. 19, 2013

Related U.S. Application Data

(60) Provisional application No. 61/605,225, filed on Mar. 1, 2012.

(30) Foreign Application Priority Data

Mar. 1, 2012 (EP) ..................... 12001394

(51) Int. Cl.
*B01L 3/00* (2006.01)
*G01N 35/10* (2006.01)
*G01N 1/00* (2006.01)
*B01L 3/02* (2006.01)

(52) U.S. Cl.
CPC ............... *B01L 3/021* (2013.01); *B01L 3/0217* (2013.01); *B01L 2300/0861* (2013.01); *G01N 35/1065* (2013.01)

(58) Field of Classification Search
CPC  B01L 3/021; B01L 3/0217; B01L 2300/0861
USPC ............... 73/864.01, 864.14, 864.17, 864.18; 422/500–501, 511, 524–526
See application file for complete search history.

(56) References Cited

U.S. PATENT DOCUMENTS

| 6,270,726 | B1 | 8/2001 | Tyberg |
| 6,324,925 | B1 | 12/2001 | Suovaniemi |
| 7,434,484 | B2 * | 10/2008 | Belgardt ............... B01L 3/0279 73/864.14 |
| 2002/0001545 | A1 * | 1/2002 | Cronenberg et al. ......... 422/100 |
| 2006/0123929 | A1 * | 6/2006 | Suovaniemi .......... B01L 3/0217 73/863.32 |

FOREIGN PATENT DOCUMENTS

| DE | 19845950 C1 | 3/2000 |
| DE | 102004003433 B4 | 3/2006 |

* cited by examiner

*Primary Examiner* — Peter Macchiarolo
*Assistant Examiner* — Anthony W Megna Fuentes
(74) *Attorney, Agent, or Firm* — Arnold & Porter LLP; Todd A. Lorenz

(57) ABSTRACT

The invention relates to a pipetting device for pipetting at least one fluid laboratory sample into at least one pipetting vessel, said device having a main body extending along an axis direction, at least one connecting section, to which at least one pipetting vessel can be connected by an at least partially axial connecting movement along the positive axis direction, wherein the at least one connecting section is connected to the main body so as to be movable at least in the axis direction, a spring mechanism, by which the at least one connecting section is supported with spring loading on the main body at least in a first operating state of the pipetting device, such that the at least one connecting section, during the connecting movement, can perform a spring-assisted deflection movement along the positive axis direction, wherein an auxiliary mechanism is provided on the pipetting device and is designed to act on the deflection movement of the at least one connecting section in at least a second operating state of the pipetting device, wherein the pipetting device is designed such that the user can alternately put it into the first operating state or the second operating state. The invention further relates to a multi-channel pipetting device.

17 Claims, 4 Drawing Sheets

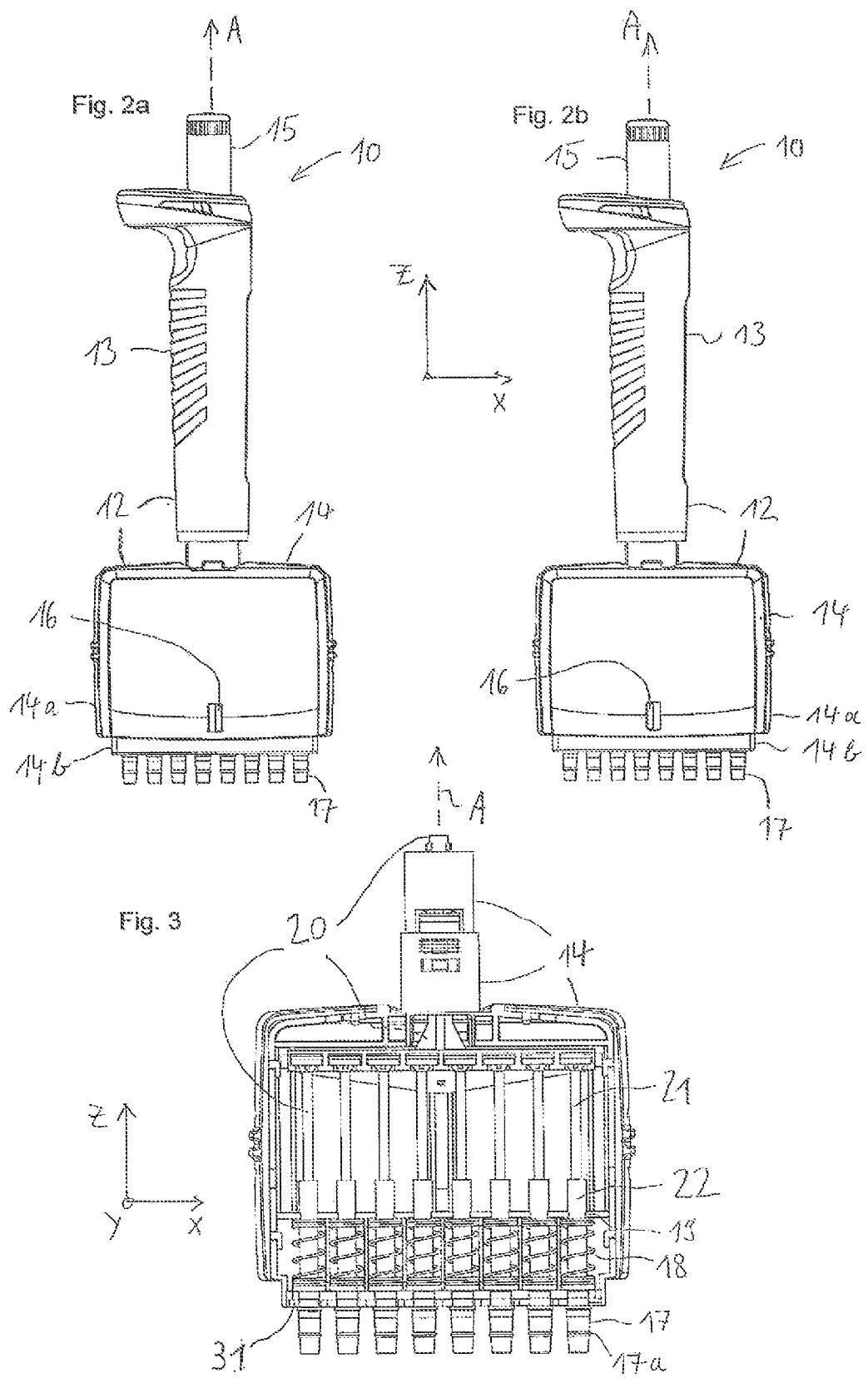

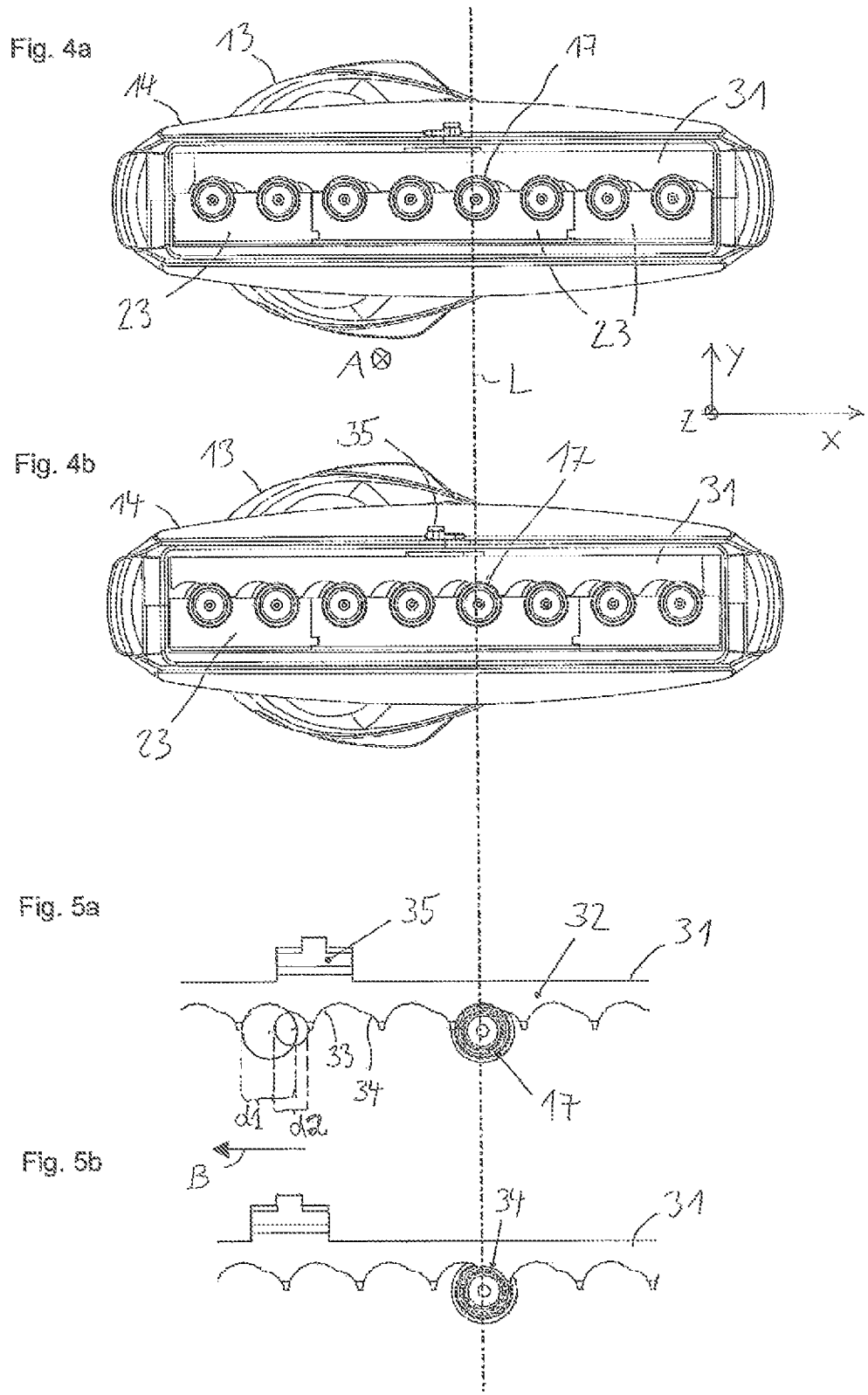

PIPETTING DEVICE AND MULTI-CHANNEL PIPETTING DEVICE

The invention relates to a pipetting device and to a multi-channel pipetting device.

Pipetting devices of this kind are customarily used in medical, biological, biochemical, chemical and other laboratories. They are used in the laboratory for the purpose of transporting and transferring fluid samples with small volumes, in particular for precise dosing of the samples. In pipetting devices, liquid samples, for example, are sucked by means of a vacuum into pipette vessels, e.g. pipette tips, are stored there, and are then released from these again at the target location.

The pipetting devices include, for example, hand-held pipettes and dispensers. A pipette is understood as an appliance in which, by means of a movement mechanism which is assigned to the appliance and which can in particular have a piston, a sample that is to be pipetted can be sucked into a pipetting vessel connected to the pipette. In an air-cushion pipette, the piston is assigned to the appliance and, situated between the sample to be pipetted and the end of the piston, there is an air cushion which is expanded when the sample is taken up info the pipetting vessel, as a result of which the sample is sucked by means of a vacuum into the pipetting vessel. A dispenser is understood as an appliance in which, by means of a movement mechanism which can in particular have a piston, a volume that is to be pipetted can be sucked into a pipetting vessel connected to the dispenser, wherein the movement mechanism is assigned at least partially to the pipetting vessel, e.g. by the piston being arranged in the pipetting vessel. In the dispenser, the end of the piston is situated very near the sample that is to be pipetted or in contact with it, for which reason the dispenser is also referred to as a direct displacement pipette.

In a pipetting device, the sample quantity released by a single actuation can correspond to the sample quantity sucked into the appliance. However, provision can also be made that a received sample quantity corresponding to several release quantities is released again in stages. Moreover, a distinction is made between single-channel pipetting devices and multi-channel pipetting devices, wherein single-channel pipetting devices contain only a single releasing/receiving channel, and multi-channel pipetting devices contain several releasing/receiving channels, which in particular permit the parallel release or take-up of several samples. Pipetting devices can in particular be operated manually, i.e. can involve the movement mechanism being driven by the user, and/or they can in particular be operated electronically.

Examples of hand-held pipettes are the Eppendorf Reference® and the Eppendorf Research® from Eppendorf AG, Hamburg, Germany; an example of a hand-held dispenser is the Multipette® plus from Eppendorf AG; an example of a hand-held electronic pipette is the Eppendorf Xplorer® from Eppendorf AG; examples of hand-held electronic dispensers are the Multipette Stream® and Xstream® from Eppendorf AG.

Pipette tips are usually stored in containers where they are inserted into a plate with holes, and the tip thus hangs free and cannot be contaminated. The plugging-on of the pipette tips usually takes place in a procedure in which the connecting section of the pipette, which connecting section is normally designed as a working cone and on which the pipette tip in particular is plugged, is placed onto the pipette tip. Here, the pipette tip is preferably plugged on only to such an extent that it sits securely on the working cone. At the same time, it is preferred that the tip is not plugged on with too much force, so as to avoid damage, and so as not to unnecessarily increase the plug-on force or ejection force needed to plug on or eject the pipette tip. If the pipette tip has to be changed, the ejector mechanism provided in most cases on the pipette is actuated by the operator, and the pipette tip is ejected. Here, the plug-on force has to be overcome by the ejector mechanism. Since the ejector mechanisms in most cases transmit the actuation force of the user, there are corresponding gears for transmitting the force as effectively as possible, or in a potentiated manner, to the pipette tip, for example as described in DE 198 45 950 C1.

In order to reduce the plug-on forces and assure the user that the pipette tip sits securely on the working cone, there are corresponding mechanisms for limiting the plug-on forces. One such mechanism is described in DE 10 2004 003 433 B4. Here, the working cones are mounted on springs in the housing. During the plugging-on of the pipette, the working cone is moved to the housing or info the housing when a defined force threshold is exceeded. The working cone then gives way to the plug-on force and performs a deflection movement. The force threshold is chosen such that the pipette tip is fixed securely on the working cone. At the same time, the plug-on force of the pipette tip is limited by the yielding or deflection of the working cone, and this has a positive effect on the ejection behaviour of the pipette tip. A pipetting device that is operated in a spring-mounted operating state of this kind requires less ejection force and is therefore particularly ergonomic.

However, in many situations, or depending on the individual user, the plug-on force defined on the pipetting device by means of the spring mechanism is not suitable for producing the connection between pipetting device and pipetting vessel in the desired manner.

The object of the invention is to make available a pipetting device and a multi-channel pipetting device which can be used more flexibly and which in particular offers greater flexibility in terms of the plug-on force between pipetting vessel (e.g. a pipette tip) and pipetting device.

According to the invention, this object is achieved by the pipetting device according to Claim 1 and the multi-channel pipetting device according to Claim 15. Preferred embodiments in particular are the subject matter of the dependent claims.

The auxiliary mechanism of the pipetting device according to the invention affords the user the advantage that he is not only able to use the first operating state of the pipetting device, in which a defined plug-on force is defined on the appliance by means of the spring mechanism in particular, but can alternatively bring about at least one second operating state, in which the auxiliary mechanism acts on the axial mobility of the at least one connecting section, in particular counteracts the axial mobility of the at least one connecting section, and in particular additionally counteracts the action of the spring mechanism. The pipetting device according to the invention can therefore be used more flexibly.

The pipetting device is preferably designed such that the at feast one connecting section and/or one of these connecting sections and/or each of these connecting sections, independently of the respective other connecting sections, can perform an axial deflection movement between a start position and a first end position in the first operating state. The first end position is preferably defined by a stop on the main body and/or on an ejector mechanism of the main body, which stop is abutted, at the end of the deflection movement, by a pipetting vessel connected to the connecting section. In this way, in the first operating state, the plug-on force of a pipetting vessel onto a connecting section is preferably defined by the spring mechanism. The first operating state is preferably such that the plug-on force is defined by the configuration of the pipetting device, in particular of the spring mechanism, and in particular cannot be influenced by the user. The operation of pipetting devices in the first operating state is functional and ergonomic, since the plug-on force is predefined such that it is not higher than is necessary for the pipetting vessels to bear tightly on the connecting section. Pipetting devices as described in DE 10 2004 003 433 B4 can be operated only in the first operating state, not alternately in the second operating state.

The pipetting device is also preferably designed such that the at least one connecting section and/or one of these connecting sections and/or each of these connecting sections, independently of the respective other connecting sections, can perform basically no axial deflection movement in the second operating state, or can perform an axial deflection movement between a start position and a second end position, where this second end position is different from the first end position. In particular, in the second operating state, a pipetting vessel connected to the connecting section preferably does not abut against a stop of the main body and/or of an ejector mechanism of the main body. In this way, in the second operating state, the plug-on force of a pipetting vessel onto a connecting section is preferably defined by the auxiliary mechanism and/or the user. The second operating state is preferably such that the plug-on force can be influenced by the user and in particular is not defined by the configuration of the pipetting device.

The auxiliary mechanism preferably has at least one auxiliary element which is arranged movably on the pipetting device such that it can be moved by the user at least between a first position and a second position on the pipetting device by an auxiliary movement, wherein the pipetting device is located in the first operating state in the first position, and wherein the pipetting device is located in the second operating state in the second position. The user himself initiates the auxiliary movement and thus decides whether he would like to operate the pipetting device in the first operating state or in the second operating state. A configuration of this kind is easy to implement and compact.

The at least one auxiliary element is preferably arranged, in the first operating state of the pipetting device, such that the at least one connecting section is supported on the spring mechanism.

The auxiliary mechanism can be designed such that the at least one auxiliary element is driven manually by the user, in order to perform the auxiliary movement. A configuration of this kind is easy to implement and compact. The auxiliary mechanism can also be designed such that the at least one auxiliary element, during the auxiliary movement, is driven by a drive mechanism that can be provided on the pipetting device. Preferably, the pipetting device or the multi-channel pipetting device has a drive mechanism in order to perform the auxiliary movement, in particular to start it electrically and/or drive it electrically. This drive mechanism is preferably operated electrically. It can have an actuator and/or an electric motor. It can in particular have a piezoelectric element, a synchronous motor or a step motor. It can also have a gear mechanism with which, in particular, the movement of the drive mechanism is transmitted info this auxiliary movement. Preferably, an electrical control mechanism of the pipetting device or of the multi-channel pipetting device is provided by which the drive mechanism is controlled automatically. In this case, provision is made in particular that the user can control this electrically driven auxiliary movement, in particular start it or reverse it, by actuating an actuation element.

The auxiliary mechanism is preferably designed such that the auxiliary movement is directed at least partially perpendicularly with respect to the axis direction. In this way, the at least one auxiliary element can be arranged such that it can be introduced at least in part into the at least partially or completely axially directed movement trajectory of the deflection movement of the at least one connecting section. Moreover, it is thus possible to ensure that the at least one auxiliary element can be brought laterally onto the at feast one connecting section, as a result of which less space is needed sin the axial direction on the pipetting device for the auxiliary movement. In particular, the auxiliary element does not have to be brought axially from above into the second position, which would require the user to disassemble the pipetting device in a relatively time-consuming manner into parts of the pipetting device that lie axially one above the other.

The auxiliary movement is preferably directed substantially perpendicularly with respect to the axis direction. In this way, a simple construction is possible in which the at least one auxiliary element can be introduced at least in part info the at least partially or completely axially directed movement trajectory of the deflection movement of the at least one connecting section, wherein minimal space is needed in the axial direction.

Preferably, the at least one auxiliary element is mounted movably an the main body and in particular connected movably, and in particular is not provided separately from the pipetting device. This corresponds to the first preferred embodiment of the invention. In particular, the at least one auxiliary element is connected to the pipetting device in the first and second operating state, in particular connected thereto in all operating states of the pipetting device. This permits simple and ergonomic operation of the pipetting device. During correct operation, no provision is then made that the auxiliary element mounted on the pipetting device is removed therefrom. However, it is possible that the pipetting device can be disassembled for maintenance purposes, when no operation is intended, in such a way that the auxiliary element is also removed or removable.

Preferably, the auxiliary mechanism has a guide mechanism with which the auxiliary movement of the at least one auxiliary element is guided on the pipetting device. The guide mechanism or the at least one auxiliary element can have at least one guide element, in particular a rail element, or at least one guiding auxiliary element, in particular a rail slide element. The guide element can be arranged on the pipetting device or on the auxiliary element. Complementary to this, the guiding auxiliary element can be arranged on the auxiliary element or on the pipetting device.

The auxiliary mechanism can have a control element by which the auxiliary mechanism can be controlled by the user, in particular by means of a control movement by the user. The control element can be a slide element, a rotary element or a deflector element by which the auxiliary movement can be effected, by means of the control element being pushed and/or turned or pivoted, and/or deflected, in particular pressed or pulled. Preferably, the auxiliary mechanism has a fixing mechanism, in particular a latch mechanism, by which the at least one auxiliary element is fixed, in particular latched, at least in the first position and/or at least the second position. The latch mechanism can be designed such that the at least one auxiliary element in the respective latched position is secured against inadvertently shifting, e.g. on account of impacts or vibrations. It is also possible that the latching action serves to confirm the positioning to the user, particularly if a securing of the position is already achieved in another way.

The auxiliary mechanism can be designed such that this control movement is transmitted directly to the at least one auxiliary element, for example by means of the control element being connected rigidly to the at least one auxiliary element, i.e. particularly in such a way that it cannot be released without destruction.

The auxiliary mechanism can also be designed such that the control movement is transmitted indirectly to the at least one auxiliary element, for example by means of the control element being connected to the at least one auxiliary element by a coupling mechanism. The coupling mechanism can have a gear mechanism, by means of which the control movement of the control element is transmitted to the at least one auxiliary element in order to effect the auxiliary movement.

The auxiliary movement is preferably a translation movement. In this way in particular, the auxiliary mechanism can be designed simply as a locking mechanism in which the auxiliary element engages with a translation movement in the preferably axial movement trajectory of the deflection movement of the at least one connecting section. However, the auxiliary movement can also be completely or partially a rotation movement. For example, provision can be made that the at least one auxiliary element is pivoted between the first position and the second position. In this way in particular, the auxiliary mechanism can be designed simply as a locking mechanism in which the auxiliary element engages with a rotation movement in the movement trajectory of the at least one connecting section. The auxiliary movement can also be a movement combining translation and rotation, e.g. with a helical course.

Preferably, the auxiliary mechanism is designed as a locking mechanism, by means of which the deflection movement is blocked substantially completely in the second operating state. It is possible that, in the second operating state, there is a slight freedom of movement in the axial direction of the connecting section on the main body. Preferably, the auxiliary mechanism is designed such that, in the second operating state, there is substantially no freedom of movement in the axial direction of the connecting section on the main body.

Preferably, the at least one auxiliary element is a bolt element, to which the at least one connecting section is locked in the second operating state and from which it is unlocked in the first operating state. It is possible that the auxiliary mechanism is designed in such a way that, in the second operating state, only some of a plurality of connecting sections are optionally influenced in terms of their axial mobility, in particular locked. In the second operating state, the at least one bolt element is preferably mounted on the main body in such a way that it is not movable at least in the positive axis direction with respect to the main body and in particular can serve as abutment for the plug-on force. However, the at least one bolt element can be movable in the negative axis direction with respect to the main body, for example if it is mounted on an ejector element of the ejector mechanism.

The bolt element is preferably a bar element, which extends in particular along a straight direction, and in particular is arranged on the pipetting device such that this direction runs at an angle of other than 0° to the axis direction, in particular substantially perpendicularly with respect to the axis direction. The bar element is preferably arranged displaceably on the pipetting device.

Particularly preferably, the mechanism is designed as a locking mechanism. This permits a particularly simple construction of the device. Preferably, the at least one connecting section has at least one first engaging section and the bolt element has at least one second engaging section, wherein the at least one first engaging section and the at least one second engaging section do not engage in each other in the first operating state, and the at least one first engaging section and the at least one second engaging section do engage in each other in the second operating state and are arranged in a locking position. In the locking position, the at least one connecting section is arranged on the main body so as to be substantially axially immovable.

Preferably, the at least one first engaging section is a recessed section of the connecting section, and the at least one second engaging section is a projecting section of the bolt element. The projecting section is preferably arranged perpendicularly with respect to the axis direction.

Preferably, the bar element has a plurality N of engaging sections, in particular projecting sections, wherein preferably $17>N>1$, and preferably N is chosen from the group of numbers $\{4, 8, 12, 18, 24, 32\}$. Preferably, the bar element has at least one recess and preferably a plurality N1 of recesses. The at least one recess is preferably designed in such a way that the at least one connecting section is axially movable if it is arranged, preferably in the first operating state, at least partially in the at least one recess. Preferably, this at least one recess of the bar element has a circular or arc-shaped contour.

This recess cars also be designed such that a first recess area has a circular or arc-shaped contour with a first radius $r1$, and a second recess area has a circular or arc-shaped contour with a second radius $r2$. The first recess area and the second recess area preferably form a contiguous recess of the bar element, wherein a connecting section is arranged in the first recess area in the first operating state, and a connecting section is arranged at least partially in the second recess area in the second operating state, wherein the connecting section in the second recess area bears or engages on an edge section of the second recess area. An engaging section of the bar element is preferably formed in such a way that an inner edge section of a recess is designed as engaging section, in particular projecting section.

Preferably, the at least one connecting section is cone-shaped, preferably widening in the direction of the main body, measured in the direction perpendicular to the axis direction. The connecting section is preferably designed in such a way that a complementary connecting section of a pipetting vessel can be plugged onto the connecting section and can be fixed there by clamping.

The at least one auxiliary element can be designed as a spacer element which substantially completely blocks, limits or inhibits the mobility of at least one connecting section, since the at least one connecting section is supported on the spacer element in the second operating state and in particular is not supported on the spring mechanism. In the second operating state, the spacer element is preferably arranged on the main body such that it abuts or bears on the main body.

Preferably, the auxiliary mechanism is designed such that, in the second operating state, the force F for deflecting the connecting section from its start position is greater in the second operating state than in the first operating state. In the second operating state, the auxiliary mechanism acts by interaction on the axial mobility of the at least one connecting section. Preferably, the at least one connecting section has at least one first interaction section, and the at least one auxiliary element, in particular bolt element, has at least one second interaction section, wherein the at least one first interaction section and the at least one second interaction section do not interact with each other in the first operating state, and the at least one first interaction section and the at least one second interaction section do interact with each other in the second operating state and thus act on the deflection movement, in particular by counteracting the latter, such that in particular the force F for deflecting the connecting section from its start position in the second operating state is greater than in the first operating state.

In particular, the auxiliary mechanism can have a second spring mechanism, which can have at least one spring element. This at least one spring element can have a substantially linear force/travel characteristic or can have, at least in part, a nonlinear force/travel characteristic. The deflection movement moves the at least one connecting section from a start position to an end position, wherein the end position of the at least one connecting section is arranged nearer the main body than in its start position.

The interaction can be such that the axial mobility of the at least one connecting section in the second operating state is completely blocked, i.e. locked, is spatially limited, or is inhibited, or in particular is so limited that the force F for deflecting the connecting section from its start position in the second operating state is different, preferably greater, than in the first operating state. Provision can be made that a predetermined distance d of the deflection movement, in particular the distance between start position and end position, of the at least one connecting section from its start position in the second operating state can be overcome by a force F2 that is greater than the force F1 in the first operating state, wherein in particular F2>f*F1, and f is a factor with preferably 1.5<f<20.

The auxiliary mechanism is preferably designed such that the force F is adjustable, in particular adjustable by the user. For this purpose, the auxiliary mechanism can have an adjustable spring mechanism of which the force-travel relationship is adjustable, for example by being able to modify a pretensioning of a spring element. In the second operating state, the adjustable spring mechanism is preferably arranged parallel to the spring mechanism and in particular acts parallel to and in addition to this spring mechanism. The pipetting device can have an electrical control mechanism and/or in particular a user interface mechanism, wherein preferably the force F can be adjusted electrically by means of the control mechanism.

The control mechanism can have electric circuits, in particular integrated circuits, and/or can have a microprocessor and/or a CPU, data memories and/or program memories. The control mechanism can be controlled by a program code, which in particular can be designed to control the auxiliary movement according to a control program.

The user interface mechanism can be or can have an actuation mechanism, which can have at least one actuation element, e.g. a control button. The user interface mechanism can also have an indicator element, e.g. a display, in order to show the user information in particular concerning the operating state and/or operating parameters of the pipetting device.

Preferably, the pipetting device is designed as a multi-channel pipetting device. For this purpose, the pipetting device preferably has a plurality N of connecting sections, wherein preferably 17>N>1, and preferably N is chosen from the group of numbers {4, 8, 1.2, 18, 24, 32}. The connecting sections are preferably oriented equidistantly along a straight line and are arranged next to each other. The distance is preferably such that several samples can be pipetted simultaneously from or info a standard microtitre plate. In a standard microtitre plate with 98 wells (see ANSI/SBS 4-2004), the distance is preferably 9 mm, and, in a microtitre plate with 384 wells, the distance is preferably 4.5 mm. Other intervals can be chosen, e.g. depending on the arrangement of the sample vessels or the type of sample vessel.

It is also possible, and provision is preferably made, that the multi-channel pipetting device has an adjustment mechanism for adjusting the distance between the connecting sections. In the case of N>2, the distance between adjacent connecting sections is preferably always constant, and therefore the distances are preferably adjusted simultaneously. The adjustment mechanism can be designed for stepless adjustment, or for adjustment in a predefined number of different and discrete distances. The adjustment mechanism can be driven mechanically, in particular manually, and/or can be driven electrically. By means of the adjustment mechanism, a multi-channel pipetting device can be easily adapted by the user for pipetting with a desired multiple-sample container, in particular a microtitre plate, and can in particular be used for use with a large number of multiple-sample containers.

A multi-channel pipetting device preferably has a movement mechanism for moving a plurality N of pistons, which can be moved by a single actuation movement, either manually driven or mechanically or electrically driven.

Moreover, according to the invention, a multi-channel pipetting device is proposed for pipetting at least one fluid laboratory sample into at least one pipetting vessel, said device having:—a main body extending, in particular extending at least in part or extending substantially completely, along an axis direction,—at least two connecting sections, to which at least two pipetting vessels can be connected by an at least partially axial connecting movement along the positive axis direction, wherein the at least two connecting sections are connected to the main body so as to be movable at least in the axial direction,—a spring mechanism, by which the at least two connecting sections are supported with spring loading on the main body at least in a first operating state of the pipetting device, such that the at least two connecting sections, during the connecting movement, can perform a spring-assisted deflection movement along the positive axis direction, wherein an auxiliary mechanism is provided on the pipetting device and Is designed to be at least partially separable from the main body and is designed to counteract the deflection movement of the at least two connecting sections in at least a second operating state of the pipetting device in addition to the action of the spring mechanism, wherein the pipetting device is designed such that the user can alternately put it into the first operating state or the second operating state, and wherein preferably the auxiliary mechanism, in the first operating state, is separated at least partially from the pipetting device and, in the second operating state, is not separated from the pipetting device. The auxiliary mechanism can have at least one auxiliary element which, in the first operating state, is separated at least partially from the pipetting device and, in the second operating state, is not separated from the pipetting device. By means of such an arrangement, it is possible in particular for a standard pipetting device to be retrofitted, as a result of which a pipetting device having the features of the present invention can be obtained.

In such a pipetting device, the second operating state can easily be produced by the user such that at least one auxiliary element or all the auxiliary elements of the pipetting device are arranged on the pipetting device in such a way that they counteract the deflection movement of the at least two connecting sections additionally to the action of the spring mechanism, in particular they substantially completely block the axial mobility of the at least two connecting sections.

Preferred embodiments that are described here for the pipetting device can also be applied in the multi-channel pipetting device.

The at least one separate auxiliary element can be designed as a spacer element which substantially completely blocks, or at least inhibits, the axial mobility of the at least two connecting sections. The spacer element can have at least one U-shaped transverse section, measured perpendicularly with respect to the axis direction, such that it can be easily transposed into the second position in a direction of the auxiliary movement perpendicular to the axis direction.

Provision can be made that the spring mechanism can be removed at least partially or completely from the main body. Preferably, at least one spring element of the spring mechanism is removed by the user before the separate auxiliary element is transposed into the second position.

The pipetting device and the multi-channel pipetting device are preferably each designed: hand-held, i.e. held by a hand, of the user;—as a laboratory robot, in which case the (multi-channel) pipetting device is not hand-held but instead held by a holding section of the laboratory robot or a transporting/lifting mechanism;—manually operated;—electrically operated;—as air-cushion pipette;—as direct displacement pipette.

Preferably, the pipetting device or the multi-channel pipetting device has a displacement mechanism for gas cushion displacement, which mechanism is arranged on the main body so as to be movable along the axis direction. The displacement mechanism has a movement mechanism, which can have one or more pistons. The at least one piston serves to ensure that, in at least one cylinder area of the pipetting device or of the multi-channel pipetting device, at least one air cushion is expanded (on aspiration of at least one sample) or compressed (on non-gravitational ejection of at least one sample).

Preferably, the pipetting device or the multi-channel pipetting device has an ejector mechanism. The ejector mechanism serves to release the at least one pipette tip from the at least one connecting section. It preferably has an ejector assigned to the at least one connecting section or to all the connecting sections, wherein the at least one connecting section and the ejector are movable relative to each other, and it has a drive mechanism operatively connected to the ejector and/or to the at least one connecting section for the relative movement of the ejector and the at least one connecting section. To release a pipetting vessel from the pipetting device, an ejection force is required, which has to act on the pipetting vessel. Preferably, the ejector mechanism of a pipetting device, in particular the ejector, is driven manually, such that the ejection force is applied mechanically by the user. However, it is also possible, and preferable, that this ejection force is applied electrically. Preferably, the ejector mechanism of an electrical pipetting device, in particular the ejector, is driven electrically, in particular by the pipetting device having an electrical drive.

The spring mechanism is preferably designed such that, in the second operating state in particular, there is a constant predefined plug-on force, which depends on the tensioning or pretensioning of at least one spring element of the spring mechanism and on the distance travelled by the at least one connecting section in the deflection movement until the pipetting vessel abuts against a stop of the main body. Provision is preferably made that the spring mechanism is designed and, if appropriate, pretensioned in such a way that the pipette tip abuts against the stop exactly when it is sitting with the desired plug-on force on the connecting section. The plug-on force is such that the pipette tip sits securely and sealingly on the connecting section. According to one embodiment, the spring element is exchangeable and/or a mechanism is present for adjusting the pretensioning of the spring element. In this way, it is possible to adapt the plug-on and ejection forces to differently shaped or dimensioned pipette tips. The range of use of the pipetting device is extended in this way. This adjustment mechanism is preferably different from the auxiliary mechanism. The adjustment mechanism can vary the predefined plug-on force with which a pipetting vessel preferably in a first operating state can be plugged onto a connecting section. Preferably, each connecting section is supported on the main body via a separate spring element.

Preferably, the stop is connected rigidly to the main body. According to another embodiment, the stop is axially movable with respect to the connecting section, and a limiting means connected rigidly to the main body is present for limiting the axial movement of the stop towards the main body. It is likewise possible, and preferable, that the stop is formed on the ejector.

Preferably, the at least one connecting section is supported directly on a spring element of the spring mechanism. The connection of the at least one connecting section to a displacement mechanism connected rigidly to the main body can be provided by means of a flexible connection, e.g. with the aid of a flexible hose or a telescoping tube connection. Preferably, the at least one connecting section is connected rigidly to a displacement mechanism, e.g. to at least one cylinder of a piston/cylinder unit that is axially movable with respect to the main body. The displacement mechanism is then moved with the at feast one connecting section. The movement of the displacement mechanism can be compensated by the drive mechanism for the displacement mechanism. According to one embodiment, the at least one cylinder is supported on the main body via the spring element, such that the at least one connecting section is cushioned indirectly via the at least one cylinder.

Preferably, the main body has an upper part and a lower part. The main body extends, in particular extends at least in part, or extends substantially completely, along an axis direction. This allows that the at least one connecting section, during the connecting movement, can perform a spring-assisted deflection movement along the positive axis direction. However, the main body, in particular the upper part and/or the lower part, can have at least one section, which does at least partially, or completely, not extend in parallel to the axis direction. Such a section can extend along an inclined direction, which encloses an angle larger than Null with the axis direction. For example, said section can be configured to provide a user interface of the pipetting device. The upper part can have a grip section. The upper part and/or the lower part can have a user interface, in particular at least one control element. The user interface can include a display and/or input elements, e.g. at least one button, switch or wheel. The upper part and/or the lower part can have a control element, in particular an electrical control element, for controlling the auxiliary mechanism or the auxiliary element. The auxiliary mechanism is preferably arranged on the lower part. The control element can be arranged on the lower part, which permits a simple design of the auxiliary mechanism, or can be arranged on the upper part, which in particular is a preferred solution for an electrical control element and/or an electrically operated auxiliary mechanism. This control element is preferably arranged on the upper part, in order to permit a more flexible and/or more comfortable use of the pipetting device or multi-channel pipetting device.

The lower part is preferably designed to be removed from the upper part by the user and then attached again, this being referred to as an exchangeable lower part. The upper part and the lower part are preferably releasable and connectable, preferably via a bayonet coupling, in a preferably axial direction. Preferably, the lower part also has the spring mechanism and/or preferably at least part of the ejector mechanism for releasing the pipetting vessel from the pipetting device. The lower part can also have a displacement mechanism, which can have at least one piston element. The upper part can have the at least one drive mechanism for driving at least one piston and/or an ejector mechanism.

The at least one displacement mechanism is preferably designed to be able to pipette a predetermined maximum volume. This maximum volume is measured such that pipetting vessels of at least one type, in particular pipetting tips, can be filled up to their maximum nominal volume by pipetting. Typical nominal volumes of commercially available pipetting tips are, for example, 10 µl, 20 µl, 100 µl, 200 µl, 300 µl, 1000 µl, 1250 µl, 2500 µl, 5 ml, 10 ml (µl: microliter; ml: milliliter).

Further preferred embodiments of the spring mechanism and of the pipetting device or of the multi-channel pipetting device, in particular as regards their functionality in the first operating state, are described in DE 10 2004 003 433 B4. Said document is hereby incorporated by reference into the present disclosure of the invention.

Further preferred embodiments of the pipetting device according to the invention and of the multi-channel pipetting device according to the invention will become clear from the following description of the illustrative embodiments in conjunction with the figures and the description thereof. Identical components of the illustrative embodiments are designated principally by the same reference signs, unless stated otherwise, or unless it appears otherwise from the context. In the figures:

FIG. 2a shows a front view of the multi-channel pipetting device from FIG. 1b in the first operating state.

FIG. 2b shows a front view of the multi-channel pipetting device from FIG. 1b in the second operating state.

FIG. 3 shows a front view of the tower part of the multi-channel pipetting device from FIG. 1b, with the front wall removed.

FIG. 4a shows a bottom view of the multi-channel pipetting device from FIG. 1b in the first operating state.

FIG. 4b shows a bottom view of the multi-channel pipetting device from FIG. 1b in the second operating state.

FIG. 5a shows a bottom view of the auxiliary element and a connecting section of the multi-channel pipetting device from FIG. 1b in the first operating state.

FIG. 5b shows a bottom view of the auxiliary element and a connecting section of the multi-channel pipetting device from FIG. 1b in the second operating state.

FIG. 6b shows the auxiliary element designed to be separable from the multi-channel pipetting device of FIG. 6a.

FIG. 6c shows a perspective view of components of the lower part of a multi-channel pipetting device according to FIG. 6a.

Figure 1A:
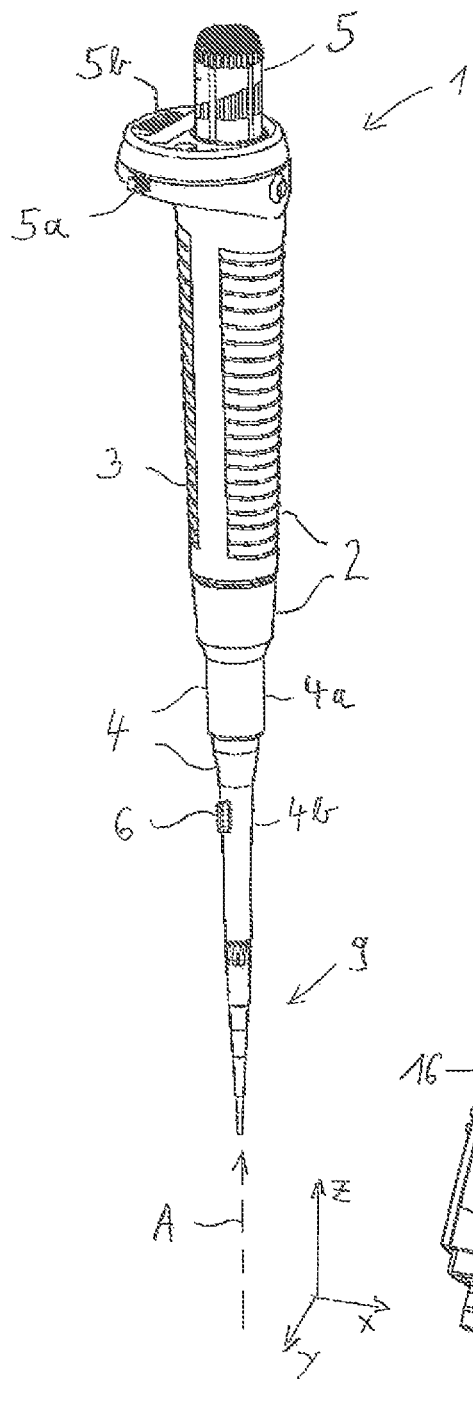
FIG. 1a shows a perspective view of a first illustrative embodiment of the pipetting device according to the invention, in the first preferred embodiment of the invention.

FIG. 1a shows the pipetting device 1 designed as a mechanical single-channel air-cushion pipette. A pipetting vessel 9 is connected in an air-tight manner to the connecting section (not visible) of the pipetting device. The pipetting device has a main body 2, which has an upper part 3 and a lower part 4. The upper part and the lower part can be connected to each other by a lock (not shown). The lower part 4 has a base section 4a mounted rigidly on the upper part of the main body. An ejector sleeve 4b for ejecting the pipetting vessel is mounted with spring loading on the base section 4a.

This is a single-button pipette with a combination control button 5. The control button 5 has several functions. It is rotatable about the axis direction A, as a result of which, when the spring-mounted release button 5a is pressed, a target pipetting volume can be adjusted, which is shown to the user via the display 5b. In the state when not pressed, the release button ensures that the adjusted target pipetting volume is not inadvertently changed. The control button 5 is mounted with spring loading. Pressing the control button 5 causes an axially downward movement of the control button 5, specifically in the direction of the negative z-axis of the Cartesian system of coordinates along the axis direction A, and a simultaneous manual drive of a movement mechanism (not shown) which is provided in the pipetting device and has a piston which moves downwards with the control button 5 until a first intermediate stop is reached. This first movement corresponds to the pipette stroke with which the target pipetting volume arranged in the cylinder is displaced. When the pressing force applied by the user is increased further, the control button is moved farther down until a second intermediate stop is reached and, in this way, the overstroke is obtained which ensures that a sample contained in the pipetting vessel 9 is ejected completely from the pipetting vessel with a sample volume corresponding to the target pipetting volume. When the pressing force applied by the user is once again increased, the control button is moved farther down, which has the effect that the ejector sleeve 4b of the ejector mechanism of the pipetting device moves downwards, forces the pipette tip 9 out of its connection position and ejects it down the way. Once the spring-mounted control button 5 is let go, it automatically moves back to the starting position.

In the first operating state in the pipetting device 1, the connecting section (not shown) of the pipetting device 1, designed as a working cone, is mounted with spring loading on the base section 4a of the lower part of the main body via a spring mechanism (not shown) having an axially oriented helical spring (not shown). The connecting section is thus supported on the helical spring. In the first operating state, a pipette tip is connected to the working cone as follows: the pipette tip is mounted in a pipette tip holder in such a way that its hollow cone-shaped connecting section is directed upwards. The user moves the pipette from above onto the pipette tip and guides the working cone into the connecting section of the pipette. During the downwardly directed movement of the pipette, the working cone in the connecting section strikes the pipette tip, the pressure on the spring-mounted working cone increases, and the working cone exposed to this pressure deflects upwards, viewed relative to the main body, until the upper edge of the pipette tip strikes a fixed stop of the main body. The stop is the lower edge of the ejector sleeve 4b. As the user of the pipette presses down further against the pipette tip, there will be no further increase in the plug-on force with which the pipette tip is plugged onto the working cone of the pipette. In this first operating state of the pipetting device 1, the plug-on force is instead predefined by the spring mechanism and cannot be influenced by the user.

In the pipetting device according to the invention, however, the user has the possibility of using the control element 8 of an auxiliary mechanism to bring about a second operating state of the pipetting device 1. In the second operating state, a bolt element (not visible) is arranged on the pipetting device in such a way that the connecting section, here the working cone, is no longer supported on the spring of the spring mechanism but on the bolt element. The bolt element is mounted on the main body in such a way that it is not movable in the positive axis direction with respect to the main body and in particular serves as an abutment for the plug-on force. However, the bolt element is arranged to be movable in the negative axis direction with respect to the main body, since it is mounted on the ejector sleeve 4*b*, which is arranged to be movable with respect to the upper part 3, and to the base section 4*a* of the lower part secured thereon, in the negative axis direction. In the second operating state, therefore, the plug-on force is defined by the force with which a user presses the pipette onto the pipette tip.

The control element 6 is a slide control which is rotatable about the axis direction A and which the user can move between a first position and a second position. In the first position, the bolt element is arranged such that the first operating state of the pipette is present, and, in the second position, the bolt element is arranged such that the second operating state of the pipette is present. The user can thus choose whether he would like to use a predefined plug-on force or would like to define the plug-on force himself.

Figure 1B:
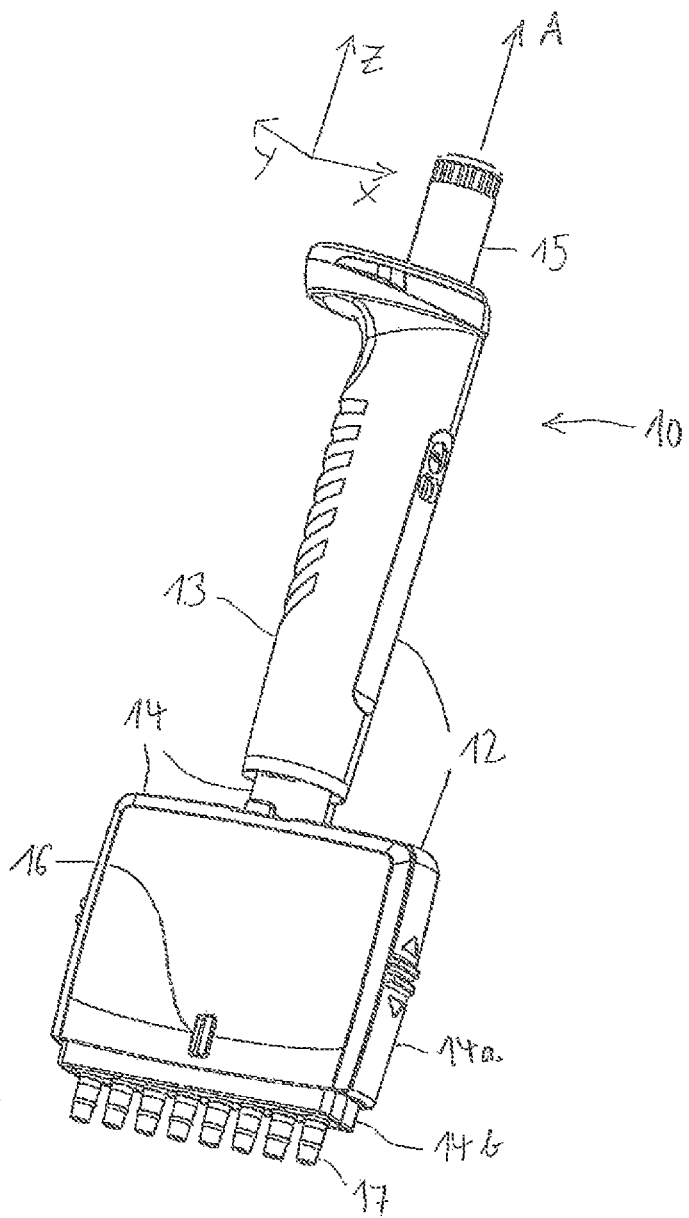
FIG. 1b shows a perspective view of a second illustrative embodiment of the multi-channel pipetting device according to the invention, in the first preferred embodiment of the invention.

FIG. 1*b* shows the pipetting device 10 designed as a mechanical 8-channel air-cushion pipette. It has a main body 12, which consists of an upper part 13 and of a lower part 14, and has a control button 15 with a functionality similar to that of the control button 5 of the pipette 1. With the ejector element 14*b* mounted on the base section 14*a* of the lower part 14 so as to be axially movable in the negative axis direction (−A), up to 8 pipette tips can be ejected simultaneously. The upper part and the lower part can be connected to each other by a lock (not shown). Up to eight pipette tips in total can be connected to the eight connecting sections 17 designed as working cones.

The 8-channel pipette has a control element 16 which is designed as a slide control and which the user can move laterally, perpendicular to the axis direction A, here parallel to the x-axis, between a first position, which is shown in FIG. 2*a*, and a second position, which is shown in FIG. 2*b*. In the first position, a bolt element of an auxiliary mechanism is arranged such that the first operating state of the 8-channel pipette is present and, in the second position, the bolt element is arranged such that the second operating state of the 8-channel pipette is present. The user can thus choose whether he would like to use a predefined plug-on force or would like to define the plug-on force himself. The function of the auxiliary mechanism is explained in more detail with reference to the subsequent figures.

FIG. 3 shows a front view of the lower part 14 of the 8-channel pipette 10, with the front wall removed and the base plate removed. An axially movable piston element 20 has eight interconnected piston rods 21, which each engage in a cylinder section 22 mounted rigidly on the lower part 14, in order to pipette up to a total of eight samples simultaneously by means of eight cylinder/piston units that can be inserted in parallel. In the illustrated first operating state of the pipetting device 10, a connecting section 17 designed as a working cone is in each case spring-mounted in the positive axis direction on a helical spring 18, which is supported on a bearing 19 of the lower part, which bearing 19 is arranged rigidly on the lower part 14. The eight connecting sections and springs are movable independently of one another, such that a number of between 1 and 8 pipette tips can be used on the 8-channel pipette. A working cone 17 has in each case an elastic sealing ring (O-ring) which is arranged around the outer wall of the cone and by which a leaktight connection of pipette tip and working cone is ensured in a particularly reliable manner. During the plugging-on of the pipette tip(s), the plug-on force is in each case automatically limited to the predefined value, since a connecting section with pipette tip is in each case moved against a spring 18 in the positive axis direction until the upper edge of the pipette tip, at the height of the underside of the bolt element 31 of the lower part 14, abuts said bolt element. This takes place in the same way as when plugging a pipette tip onto the working cone of a pipette 1 as described with reference to FIG. 1. Here, the underside of the ejector 23 (see FIGS. 4*a* and 4*b*) of the multi-channel pipette is situated at the same height as the underside of the bolt element 31, such that, during the plugging-on of the pipette tip, the latter also abuts with its upper edge against the ejector 23, which therefore likewise serves as an abutment section.

FIG. 4*a* shows a bottom view of the 8-channel pipette 10 in the first operating state. The bolt element 31 is mounted so as to be movable along the x-axis, perpendicularly with respect to the axis direction A, by means of a guide mechanism. The bolt element 31 is mounted so as to be substantially immovable parallel to the axial direction A, with respect to the lower part 14. Using the slide control 16, the user can move the bolt element between the first position, which is shown in FIG. 2*a*, FIG. 4*a* and FIG. 5*a*, and the second position, which is shown in FIG. 2*b*, FIG. 4*b* and FIG. 5*b*.

FIGS. 4*a*, 4*b* and FIGS. 5*a*, 5*b* are in each case arranged one above the other, such that the working cone 17 is arranged along the x-axis in the same position that is defined by the intersection of the line L with the x-axis, whereas the bolt element 31 is moved relative thereto along the x-axis.

In the first position, the 8-channel pipette 10 is in the first operating state, and, in the second position, the 8-channel pipette 10 is in the second operating state. In the first position, each working cone 17 is movable at least in the positive axis direction A with respect to the lower part of the main body, and, in the second position, each working cone 17 is completely blocked and immovable in the positive axis direction A with respect to the lower part of the main body.

This blocking and locking effect is obtained by virtue of the fact that, in the second position, a projecting section of the axially immovable bolt element in each case engages in a groove which is formed in each case in a connecting section 17 at the height (along the z-axis, or A) of the bolt element 31. The bolt element is a flat bar element, here with a base body 32 in the shape of a right parallelepiped. The base body 32 has several pairs of overlapping arc-shaped recesses 33, 34 which lie alongside one another in the x-direction and have a different diameter or radius. The larger recess 33 has a diameter d1. The recess 33 is designed such that, in the first position, the working cone 17 is freely movable within the recess 33. The smaller recess 34 has a smaller diameter d2, with d2<d1. The edge of the recess 34 forms the projection which, in the second position, can engage at least partially in a groove formed in the working cone and perpendicular to the axis direction A, such that the working cone, in this second position, is locked substantially free of play in the axis direction. Like the bar element itself, the projecting section has a small height h, such that the auxiliary mechanism takes up only a small space in the pipette in the axial direction. The height h, or maximum height h, of the bolt element or of the projecting section can be chosen such that preferably 0.1 mm<h<3.0 mm.

The bolt element 31 is coupled to the control element 16 by a coupling section 35 of the bolt element, such that, when a user in the present case initiates a control movement B of the control element 18, this leads directly to the same movement of the bolt element 31. The first position and the second position are in each case secured via a locking of the bolt element and/or of the control element on the main body.

A multi-channel pipetting device of this kind is particularly comfortable to operate and provides full flexibility of use in both operating states.

Figure 6A:
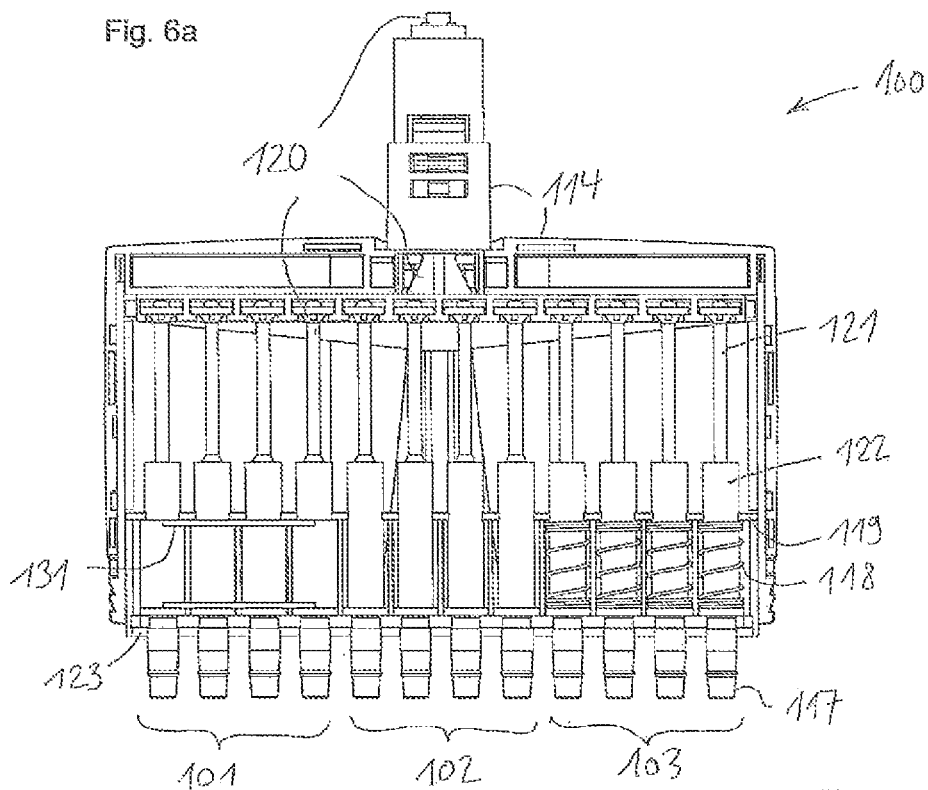
FIG. 6a shows a front view of the lower part of a multi-channel pipetting device according to the second preferred embodiment of the invention, with the front wall removed.
Figure 6B:
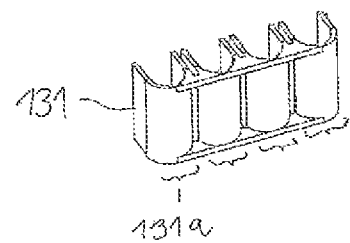
Figure 6C:
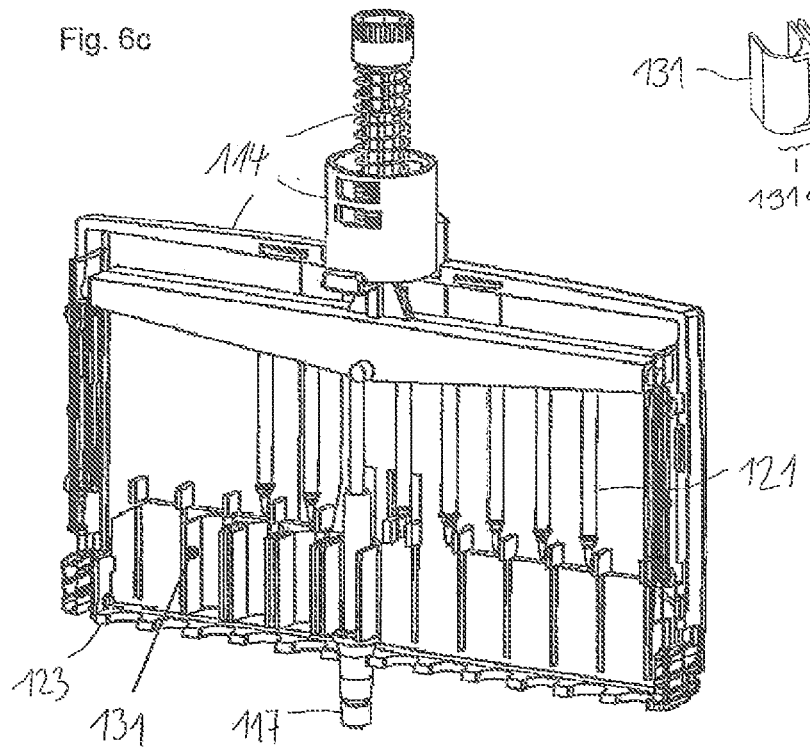

FIG. 6a shows a front view of the lower part 114 of a multi-channel pipetting device 100 (shown only in part here) according to the second preferred embodiment of the invention, with the front wall removed. At least one auxiliary element 131, comprising a total of at most three bolt elements, is not a component part of the multi-channel pipetting device 100 in a first operating state of the latter but is instead arranged separately therefrom. The multi-channel pipetting device 100 has a similar construction to the multi-channel pipetting device 10 but has a total of 12 pipetting channels with a total of 12 cylinder/piston units.

The axially movable piston element 120 has 12 interconnected piston rods 121, which each engage in a cylinder section 122 mounted rigidly on the lower part 114, in order to pipette up to a total of 12 samples simultaneously by means of 12 cylinder/piston units that can be inserted in parallel. In the illustrated first operating state of the pipetting device 100, a connecting section 117 designed as a working cone is in each case spring-mounted in the positive axis direction on a helical spring 118, which is supported on a bearing 119 of the lower part, which bearing 119 is arranged rigidly on the lower part 114. The 12 connecting sections and springs are movable independently of one another, such that a number of between 1 and 12 pipette tips can be used on the 12-channel pipette. A working cone 117 has in each case an elastic sealing ring (O-ring) which is arranged around the outer wall of the cone and by which a leaktight connection of pipette tip and working cone is ensured in a particularly reliable manner. During the plugging-on of the pipette tip(s), the plug-on force is in each case automatically limited to the predefined value, since a connecting section with pipette tip is in each case moved against a spring 118 in the positive axis direction until the upper edge of the pipette tip abuts on an abutment section 123 of the lower part 114. This takes place in the same way as when plugging a pipette tip onto the working cone of a pipette 1 as described with reference to FIG. 1.

The multi-channel pipetting device 100 is designed in such a way that at least one spring 118, in particular several springs 118, in the present case four springs, are removed from the multi-channel pipetting device 100 by the user before an auxiliary element is inserted such that it at least partially assumes the position in which the now removed springs 118 were arranged. An auxiliary element 131 is designed as a spacer element which, in a second operating state of the multi-channel pipetting device 100, is arranged on the latter in such a way that the spacer element is supported firmly on the main body or lower part 114, here on the bearing 119, at least in the positive axis direction, and the at least one connecting section (in the present case four connecting sections) is supported axially on the spacer element in a substantially immovable manner.

In the present case, the spacer element has four subsections 131a which are each designed to be arranged, instead of a spring 118, in the multi-channel pipetting device 100. The spacer element can generally have the same number of subsections as there are connecting sections, i.e. in the present case up to 12 subsections, or fewer subsections, in particular just one subsection or just two subsections. The user can thus choose whether to change all or only some of the connecting sections to the second operating state and thus block them.

In FIG. 6a, the four connecting sections which are assigned to the group 101 of connecting sections are axially blocked by a spacer element 131, in accordance with a second operating state. In the group 102 of connecting sections, the connecting sections are freely movable axially, since the four springs 118 were each removed, which has the effect that the connecting sections cannot find support in the positive axis direction and to this extent are not operational. In the group 103 of connecting sections, the connecting sections are mounted on springs and axially movable, in accordance with a first operating state.

The multi-channel pipetting device 100 according to the second preferred embodiment of the invention is particularly suitable for users who want a multi-channel pipetting device which has spring-mounted, movable connecting sections and which can be easily converted into a multi-channel pipetting device with at least some connecting sections that are axially immovable, since there will be at least some occasions when these users do not wish to use the first operating state.

The invention claimed is:

1. A pipetting device for pipetting at least one fluid laboratory sample into at least one pipetting vessel, said pipetting device comprising: a main body extending along an axis direction; at least one connecting section, configured to be connected to the at least one pipetting vessel by an at least partially axial connecting movement along a positive axis direction; wherein the at least one connecting section is connected to the main body so as to be movable at least parallel to the axis direction; and wherein the at least one connecting section is configured such that, by way of the connecting movement, at least one complementary connecting section of the at least one pipetting vessel is plugged into the at least one connecting section is fixed there by clamping; a spring mechanism, by which the at least one connecting section is supported with spring loading on the main body at least in a first operating state of the pipetting device, such that the at least one connecting section, during the connecting movement, is capable of performing a spring-assisted deflection movement along the positive axis direction; characterized the main body of the pipetting device comprises a stop and is a configured such that, in the first operating state, the deflection movement is performed between a start position and an end position, and at the end position of the deflection movement, the stop is abutted by an upper edge of the at least one pipetting vessel connected to the connecting section, and wherein an auxiliary mechanism is provided on the pipetting device and is configured to act on a deflection movement of the at least one connecting section in at least a second operating state of the pipetting device; and wherein the pipetting device is configured such that the pipetting device is capable of being alternately put into the first operating state or the second operating state.

2. The pipetting device according to claim 1, wherein the auxiliary mechanism has at least one auxiliary element which is arranged movably on the pipetting device such that it is capable of being moved between a first position and a second position on the pipetting device by an auxiliary movement, wherein the pipetting device is located in the first operating state in the first position, and wherein the pipetting device is located in the second operating state in the second position.

3. The pipetting device according to claim 2, wherein the auxiliary movement is directed at least partially perpendicularly with respect to the axis direction.

4. The pipetting device according to claim 2 or 3, wherein the at least one auxiliary element is mounted movably on the main body.

5. The pipetting device according to claim 2, comprising an electrical drive mechanism configured to perform the auxiliary movement.

6. The pipetting device according to claim 2, comprising an electrical control mechanism configured to control the auxiliary movement at least partially or completely electrically.

7. The pipetting device according to claim 1, wherein the auxiliary mechanism is configured as a locking mechanism, by means of which the deflection movement is blocked substantially completely in the second operating state.

8. The pipetting device according to claim 2, wherein the auxiliary element is a bolt element.

9. The pipetting device according to claim 8, wherein the at least one connecting section has at least one first engaging section and the bolt element has at least one second engaging section, wherein the at least one first engaging section and the at least one second engaging section do not engage in each other in the first operating state, and the at least one first engaging section and the at least one second engaging section do engage in each other in the second operating state and are arranged in a locking position.

10. The pipetting device according to claim 9, wherein the at least one first engaging section is a recessed section of the connecting section, and the at least one second engaging section is a projecting section of the bolt element.

11. The pipetting device according to claim 1, wherein the auxiliary mechanism is configured such that, in the second operating state, a force for deflecting the connecting section from its start position is greater in the second operating state than in the first operating state.

12. The pipetting device according to claim 11, wherein the auxiliary mechanism is configure such that the force is adjustable.

13. The pipetting device according to claim 1, which is configured as a multi-channel pipetting device.

14. A multi-channel pipetting device, for pipetting at least one fluid laboratory sample in to art least two pipetting vessels, said multi-channel pipetting device comprising: a main body extending along an axis direction; at least two connecting sections, configured to be connected to the at least two pipetting vessels by an at least partially axial connecting movement along a positive axis direction, wherein the at least two connecting sections are connected to the main body so as to be movable at least parallel to the axis direction; and wherein the at least two connecting sections are configured such that, by way of the connecting movement, at least two complementary connecting sections of the pipetting vessels are plugged onto the at least two connecting sections and are fixed there by clamping; at least in a first operating state, a spring mechanism, by which the at least two connecting sections are supported with spring loading on the main body at least in a first operating state of the pipetting device, such that the at least two connecting sections, during the connecting movement, is capable of performing a spring-assisted deflection movement along the positive axis direction; characterized in that an auxiliary mechanism is provided on the pipetting device and is configured to be at least partially separable from the main body and is configured to counteract a deflection movement of the at least two connecting sections in at least a second operating state of the pipetting device in addition to the action of the spring mechanism, wherein the pipetting device is configured such that the pipetting device is capable of being alternately put into the first operating state or the second operating state, and wherein the auxiliary mechanism, in the first operating state, is separated at least partially from the pipetting device and, in the second operating state, is not separated from the pipetting device.

15. Use of the pipetting device according to claim 1 or 14 in a medical, biological, biochemical and/or chemical laboratory.

16. The pipetting device according to claim 1, which has an ejector mechanism configured to release the at least one pipette vessel connected to the at least one connecting section from the at least one connecting section, the ejector mechanism comprising an ejector, wherein the at least one connecting section and the ejector are movable relative to each other, and wherein the stop is formed on the ejector.

17. The pipetting device according to claim 16, wherein the ejector is an ejector sleeve and the stop is a lower edge of the ejector sleeve.

* * * * *